United States Patent
Barak et al.

(10) Patent No.: US 11,944,388 B2
(45) Date of Patent: Apr. 2, 2024

(54) SYSTEMS AND METHODS FOR MAGNETIC INTERFERENCE CORRECTION

(71) Applicant: COVIDIEN LP, Mansfield, MA (US)

(72) Inventors: Ron Barak, Tel Aviv (IL); Ariel Birenbaum, Herzliya (IL)

(73) Assignee: Covidien LP, Mansfield, MA (US)

( * ) Notice: Subject to any disclaimer, the term of this patent is extended or adjusted under 35 U.S.C. 154(b) by 1133 days.

(21) Appl. No.: 16/582,587

(22) Filed: Sep. 25, 2019

(65) Prior Publication Data

US 2020/0100844 A1   Apr. 2, 2020

Related U.S. Application Data

(60) Provisional application No. 62/794,209, filed on Jan. 18, 2019, provisional application No. 62/794,435, (Continued)

(51) Int. Cl.
| | |
|---|---|
| A61B 34/20 | (2016.01) |
| A61B 5/00 | (2006.01) |
| A61B 5/06 | (2006.01) |
| A61B 6/00 | (2006.01) |
| G01B 7/004 | (2006.01) |
| G01R 31/00 | (2006.01) |

(Continued)

(52) U.S. Cl.
CPC ............ *A61B 34/20* (2016.02); *A61B 5/062* (2013.01); *A61B 5/065* (2013.01); *A61B 5/7217* (2013.01); *A61B 6/487* (2013.01); *G01B 7/004* (2013.01); *G01R 31/001* (2013.01); *H01Q 1/22* (2013.01); *A61B 2034/2051* (2016.02); *A61B 2034/2072* (2016.02); *A61B 2090/376* (2016.02)

(58) Field of Classification Search
CPC ......... A61B 34/20; A61B 5/062; A61B 5/065; A61B 2034/2051; A61B 2034/2072; G01R 31/001
See application file for complete search history.

(56) References Cited

U.S. PATENT DOCUMENTS

| | | | | |
|---|---|---|---|---|
| 5,767,669 A | * | 6/1998 | Hansen | .......... G01B 7/004 324/225 |
| 5,899,860 A | | 5/1999 | Pfeiffer et al. | |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Extended European Search Report issued in European Patent Application No. 19200249.1 dated Feb. 17, 2020, 8 pages.

(Continued)

*Primary Examiner* — Serkan Akar
*Assistant Examiner* — Amal Aly Farag
(74) *Attorney, Agent, or Firm* — Weber Rosselli & Cannon LLP

(57) ABSTRACT

Navigation systems and methods for magnetic interference correction involve antennae that generate magnetic fields at different frequencies, sensors that measure the magnetic fields, and a computing device that uses sensor measurements to determine the magnetic interference and produce accurate sensor position and orientation information.

20 Claims, 4 Drawing Sheets

Related U.S. Application Data filed on Jan. 18, 2019, provisional application No. 62/738,148, filed on Sep. 28, 2018.

(51) Int. Cl.
   *H01Q 1/22* (2006.01)
   *A61B 90/00* (2016.01)

(56) References Cited

U.S. PATENT DOCUMENTS

| | | |
|---|---|---|
| 6,016,439 A | 1/2000 | Acker |
| 6,400,139 B1 | 6/2002 | Khalfin et al. |
| 6,493,573 B1 | 12/2002 | Martinelli et al. |
| 6,701,179 B1 | 3/2004 | Martinelli et al. |
| 7,335,156 B2 | 2/2008 | Pattern et al. |
| 7,366,562 B2 | 4/2008 | Dukesherer et al. |
| 7,599,730 B2 | 10/2009 | Hunter et al. |
| 7,697,972 B2 | 4/2010 | Verard et al. |
| 7,751,865 B2 | 7/2010 | Jascob et al. |
| 7,818,044 B2 | 10/2010 | Dukesherer et al. |
| 7,840,253 B2 | 11/2010 | Tremblay et al. |
| 7,971,341 B2 | 7/2011 | Dukesherer et al. |
| 7,981,038 B2 | 7/2011 | Kanade et al. |
| 8,016,749 B2 | 9/2011 | Clerc et al. |
| 8,046,052 B2 | 10/2011 | Verard et al. |
| 8,060,185 B2 | 11/2011 | Hunter et al. |
| 8,175,681 B2 | 5/2012 | Hartmann et al. |
| 8,239,001 B2 | 8/2012 | Verard et al. |
| 8,271,069 B2 | 9/2012 | Jascob et al. |
| 8,335,359 B2 | 12/2012 | Fidrich et al. |
| 8,359,730 B2 | 1/2013 | Burg et al. |
| 8,382,372 B2 | 2/2013 | Maschke |
| 8,401,616 B2 | 3/2013 | Verard et al. |
| 8,452,068 B2 | 5/2013 | Averbuch et al. |
| 8,467,853 B2 | 6/2013 | Hunter et al. |
| 8,480,588 B2 | 7/2013 | Kanade et al. |
| 8,494,613 B2 | 7/2013 | Markowitz et al. |
| 8,549,732 B2 | 10/2013 | Burg et al. |
| 8,611,983 B2 | 12/2013 | Glossop |
| 8,611,984 B2 | 12/2013 | Greenburg et al. |
| 8,644,907 B2 | 2/2014 | Hartmann et al. |
| 8,696,548 B2 | 4/2014 | Gilboa |
| 8,696,685 B2 | 4/2014 | Gilboa |
| 8,706,184 B2 | 4/2014 | Mohr et al. |
| 8,731,641 B2 | 5/2014 | Hartmann et al. |
| 8,821,376 B2 | 9/2014 | Tolkowsky |
| 8,827,934 B2 | 9/2014 | Chopra et al. |
| 8,971,993 B2 | 3/2015 | Strommer et al. |
| 8,992,546 B2 | 3/2015 | Viswanathan et al. |
| 9,113,813 B2 | 8/2015 | Greenburg et al. |
| 9,316,713 B2 | 4/2016 | Iwadate et al. |
| 9,370,398 B2 | 6/2016 | Ladtkow et al. |
| 9,387,048 B2 | 7/2016 | Donhowe et al. |
| 9,439,623 B2 | 9/2016 | Frank et al. |
| 9,504,530 B2 | 11/2016 | Hartmann et al. |
| 9,566,043 B2 | 2/2017 | Kanade et al. |
| 9,603,668 B2 | 3/2017 | Weingarten et al. |
| 9,664,763 B2 | 5/2017 | Amthor et al. |
| 9,727,963 B2 | 8/2017 | Mintz et al. |
| 9,733,336 B2 | 8/2017 | Shen et al. |
| 9,770,216 B2 | 9/2017 | Brown et al. |
| 9,836,848 B2 | 12/2017 | Markov et al. |
| 9,848,953 B2 | 12/2017 | Weingarten et al. |
| 9,861,338 B2 | 1/2018 | Kanade et al. |
| 9,861,440 B2 | 1/2018 | Weide et al. |
| 9,888,970 B2 | 2/2018 | Strommer et al. |
| 9,918,659 B2 | 3/2018 | Chopra et al. |
| 9,956,049 B2 | 5/2018 | Shmarak et al. |
| 9,972,081 B2 | 5/2018 | Wei et al. |
| 10,010,373 B2 | 7/2018 | Canfield et al. |
| 10,039,473 B2 | 8/2018 | Zhao et al. |
| 10,058,370 B2 | 8/2018 | Danek et al. |
| 10,074,185 B2 | 9/2018 | Markov et al. |
| 10,098,565 B2 | 10/2018 | Brannan et al. |
| 10,098,566 B2 | 10/2018 | Brannan et al. |
| 10,105,185 B2 | 10/2018 | Weingarten et al. |
| 10,143,373 B2 | 12/2018 | Gilad-Gilor |
| 10,154,798 B2 | 12/2018 | Greenburg et al. |
| 10,165,928 B2 | 1/2019 | Hunter et al. |
| 10,169,875 B2 | 1/2019 | Mintz et al. |
| 10,195,464 B2 | 2/2019 | Vertatschitsch et al. |
| 10,249,036 B2 | 4/2019 | Holsing et al. |
| 10,258,413 B2 | 4/2019 | Zhai et al. |
| 10,264,947 B2 | 4/2019 | Holsing et al. |
| 10,292,619 B2 | 5/2019 | Averbuch |
| 10,328,195 B2 | 6/2019 | Krimsky |
| 10,328,280 B2 | 6/2019 | Stopek |
| 10,328,281 B2 | 6/2019 | Stopek |
| 10,335,240 B2 | 7/2019 | Grunwald et al. |
| 10,346,976 B2 | 7/2019 | Averbuch et al. |
| 10,362,963 B2 | 7/2019 | Koyrakh et al. |
| 10,373,719 B2 | 8/2019 | Soper et al. |
| 10,376,178 B2 | 8/2019 | Chopra |
| 10,391,277 B2 | 8/2019 | Rahimian et al. |
| 10,404,093 B2 | 9/2019 | Gliner et al. |
| 10,405,753 B2 | 9/2019 | Sorger |
| 10,413,272 B2 | 9/2019 | Jasperson et al. |
| 10,418,705 B2 | 9/2019 | Morgan et al. |
| 10,426,555 B2 | 10/2019 | Crowley et al. |
| 10,444,315 B2 | 10/2019 | Beck et al. |
| 10,446,931 B2 | 10/2019 | Morgan et al. |
| 10,448,861 B2 | 10/2019 | Stopek et al. |
| 10,448,862 B2 | 10/2019 | Stopek et al. |
| 10,448,886 B2 | 10/2019 | Krimsky |
| 10,470,839 B2 | 11/2019 | Krimsky |
| 10,478,162 B2 | 11/2019 | Barbagli et al. |
| 10,478,254 B2 | 11/2019 | Krimsky |
| 10,480,926 B2 | 11/2019 | Froggatt et al. |
| 10,482,599 B2 | 11/2019 | Mintz et al. |
| 10,499,992 B2 | 12/2019 | Wei et al. |
| 10,517,505 B2 | 12/2019 | Morgan et al. |
| 10,524,866 B2 | 1/2020 | Srinivasan et al. |
| 10,542,953 B2 | 1/2020 | Krimsky |
| 10,555,788 B2 | 2/2020 | Panescu et al. |
| 10,568,700 B2 | 2/2020 | Donhowe et al. |
| 10,575,907 B2 | 3/2020 | Dekel et al. |
| 10,582,914 B2 | 3/2020 | Herdina et al. |
| 10,610,306 B2 | 4/2020 | Chopra |
| 10,615,500 B2 | 4/2020 | Morgan et al. |
| 10,617,324 B2 | 4/2020 | Hunter et al. |
| 10,631,933 B2 | 4/2020 | Krimsky |
| 10,638,952 B2 | 5/2020 | Morgan et al. |
| 10,638,953 B2 | 5/2020 | Duindam et al. |
| 10,646,277 B2 | 5/2020 | Weingarten et al. |
| 10,646,283 B2 | 5/2020 | Johnson et al. |
| 10,646,284 B2 | 5/2020 | Weingarten et al. |
| 10,653,485 B2 | 5/2020 | Weingarten et al. |
| 10,660,708 B2 | 5/2020 | Weingarten et al. |
| 10,674,936 B2 | 6/2020 | Averbuch et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 2003/0013972 A1 | 1/2003 | Makin |
| 2004/0102696 A1 | 5/2004 | Govari |
| 2004/0176931 A1 | 9/2004 | Wright et al. |
| 2010/0179782 A1 | 7/2010 | Kimura et al. |
| 2012/0165660 A1 | 6/2012 | Wu |
| 2013/0303945 A1 | 11/2013 | Blumenkranz et al. |
| 2014/0035798 A1 | 2/2014 | Kawada et al. |
| 2015/0148690 A1 | 5/2015 | Chopra et al. |
| 2015/0176961 A1* | 6/2015 | Montag ............. A61B 5/062 702/94 |
| 2015/0265368 A1 | 9/2015 | Chopra et al. |
| 2015/0305823 A1 | 10/2015 | Claus |
| 2016/0157939 A1 | 6/2016 | Larkin et al. |
| 2016/0174872 A1* | 6/2016 | Govari ............. G01D 5/12 324/207.22 |

(56) References Cited

U.S. PATENT DOCUMENTS

| | | |
|---|---|---|
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0065205 A1 | 3/2017 | Ludwin et al. |
| 2017/0112576 A1 | 4/2017 | Coste-Maniere et al. |
| 2017/0209071 A1 | 7/2017 | Zhao et al. |
| 2017/0209072 A1 | 7/2017 | Oren et al. |
| 2017/0224423 A1 | 8/2017 | Suzuki |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0116722 A1 | 5/2018 | Koyrakh et al. |
| 2018/0116730 A1 | 5/2018 | Koyrakh et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2018/0335519 A1 | 11/2018 | Gliner et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CZ | 486540 | 9/2016 |
| CZ | 2709512 | 8/2017 |
| CZ | 2884879 | 1/2020 |
| EP | 2888997 A1 | 7/2015 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |
| WO | 2008110553 A2 | 9/2008 |
| WO | 2016147472 A1 | 9/2016 |
| WO | 2018081356 A1 | 5/2018 |

OTHER PUBLICATIONS

Non-Final office action issued in U.S. Appl. No. 16/576,568 dated Apr. 6, 2022.

Extended European Search Report issued in European Patent Application No. 19200227.7 dated Jun. 3, 2020, 10 pages.

\* cited by examiner

SYSTEMS AND METHODS FOR MAGNETIC INTERFERENCE CORRECTION

CROSS REFERENCE TO RELATED APPLICATION

The present application claims the benefit of and priority to U.S. Provisional Application Ser. No. 62/794,435, filed on Jan. 18, 2019, U.S. Ser. No. 62/794,209, filed on Jan. 18, 2019, and U.S. Ser. No. 62/738,148, filed on Sep. 28, 2018. The entire contents of all of which are incorporated herein by reference.

BACKGROUND

Technical Field

This disclosure relates to electromagnetic navigation systems and methods and more particularly to methods and systems for correcting magnetic interference caused by metal objects within the clinical space.

Discussion of Related Art

Electromagnetic navigation (EMN) has helped expand medical imaging, diagnosis, and treatment capabilities by enabling a location and/or an orientation of a medical device to be accurately determined while the device is within the body of a patient. One example of a medical procedure in which EMN is employed is ELECTROMAGNETIC NAVIGATION BRONCHOSCOPY® (ENB™), which includes a planning phase and a navigation phase. During the planning phase, a computed tomography (CT) scan of the chest of the patient is used to generate a virtual three-dimensional bronchial map of the patient and a planned pathway for the navigation phase. During the navigation phase, an antenna assembly radiates electromagnetic fields throughout the chest of the patient, a practitioner places electromagnetic sensors on the chest of the patient and inserts a device, e.g., a catheter, having an electromagnetic sensor into the airway of the patient, and a computing device determines a location and/or an orientation (e.g., relative to the planned pathway) of the electromagnetic sensor based on the electromagnetic fields sensed by the electromagnetic sensors.

To enable accurate determination of sensor location and/or orientation, a detailed map of electromagnetic (EM) field measurements at respective sensor locations is generated. Generating such a map, however, requires taking precise electromagnetic field measurements at many (for example, hundreds of thousands or more) locations within the expected electromagnetic volume, which is a laborious and time-consuming process that, in some cases, requires expensive machines. Also, interfering EM fields may be detected by the EM sensors and, as a result, the accuracy of the detected position and orientation of an EM sensor within the EM field suffers.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a navigation system for magnetic interference correction, including: a plurality of antennae configured to generate a plurality of magnetic fields at different frequencies. The navigation system also includes a plurality of sensors configured to measure the plurality of magnetic fields. The navigation system also includes a computing device configured to: obtain first magnetic field vector measurements from the plurality of sensors for a portion of the plurality of antennae, evaluate predetermined functions using the first magnetic field vector measurements to obtain first position and orientation information for the plurality of sensors, obtain second magnetic field vector measurements from the plurality of sensors for the plurality of antennae, and search, starting with the first position information, a simulated map for position information of the plurality of sensors such that the difference between (a) the sum of simulated magnetic field vectors corresponding to the position information and interference magnetic field vectors, which is rotated according to orientation information, and (b) the second magnetic field vector measurements are minimized. Other embodiments of this aspect include corresponding computer systems, apparatus, and computer programs recorded on one or more computer storage devices, each configured to perform the actions of the methods.

Implementations may include one or more of the following features. The navigation system where the plurality of sensors includes three patient sensors. The navigation system where the plurality of sensors further includes a catheter sensor. The navigation system where determining the plurality of interference magnetic field vectors includes determining three coordinates of an interference magnetic field vector for each of the plurality of sensors at one frequency of a magnetic field generated by one antenna of the plurality of antennae and determining a plurality of ratios for a respective plurality of other frequencies of magnetic fields generated by other antennae of the plurality of antennae. The navigation system where the plurality of antennae includes nine antennae. The navigation system where the portion of the plurality of antennae includes three antennae. The navigation system where searching the simulated map includes performing a Levenberg-Marquadt search. The navigation system further including a medical device, which generates a plurality of interference magnetic fields from eddy currents induced in the medical device by a respective plurality of magnetic fields generated by the respective plurality of antennae. The navigation system where the medical device is a fluoroscope or a robotic arm. The navigation system where the computing device is further configured to determine functions that provide a relationship between (a) magnetic field vector measurements obtained by the plurality of patient sensors and (b) position and orientation information of the plurality of patient sensors based on calibration measurements of the magnetic fields generated by a portion of the plurality of antennae at known positions and orientations of the plurality of patient sensors. Implementations of the described techniques may include hardware, a method or process, or computer software on a computer-accessible medium.

One general aspect includes a method for magnetic interference correction, including: obtaining, from a plurality of sensors, measurements of first magnetic fields generated by a portion of a plurality of antennae. The method also includes evaluating predetermined functions using the first magnetic field measurements to obtain first position and orientation information for the plurality of sensors. The method also includes obtaining second magnetic field measurements from the plurality of sensors for the plurality of antennae. The method also includes searching, starting with the first position information, a simulated map for position information of the plurality of sensors such that the difference between (a) the sum of simulated magnetic field corresponding to the position information and the interference magnetic field, which is rotated according to orientation information, and (b) the second magnetic field measurements is minimized. Other embodiments of this aspect include corresponding computer systems, apparatus, and computer programs recorded on one or more computer storage devices, each configured to perform the actions of the methods.

Implementations may include one or more of the following features. The method where the plurality of sensors include three patient sensors. The method where determining the plurality of interference vectors includes determining three coordinates of an interference vector for each of the plurality of patient sensors at one frequency of a magnetic field generated by one antenna of the plurality of antennae and determining a plurality of ratios for a respective plurality of other frequencies of magnetic fields generated by other antennae of the plurality of antennae. The method where the plurality of antennae includes nine antennae. The method where the portion of the plurality of antennae includes three antennae. The method where searching the simulated map includes performing a Levenberg-Marquadt search. The method further including determining functions that provide a relationship between (a) magnetic field vector measurements obtained by the plurality of patient sensors and (b) position and orientation information of the plurality of patient sensors based on calibration measurements of the magnetic fields generated by a portion of the plurality of antennae at known positions and orientations of the plurality of patient sensors. Implementations of the described techniques may include hardware, a method or process, or computer software on a computer-accessible medium.

Any of the above features, aspects, and embodiments of this disclosure may be combined without departing from the scope of this disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

Figure 1:
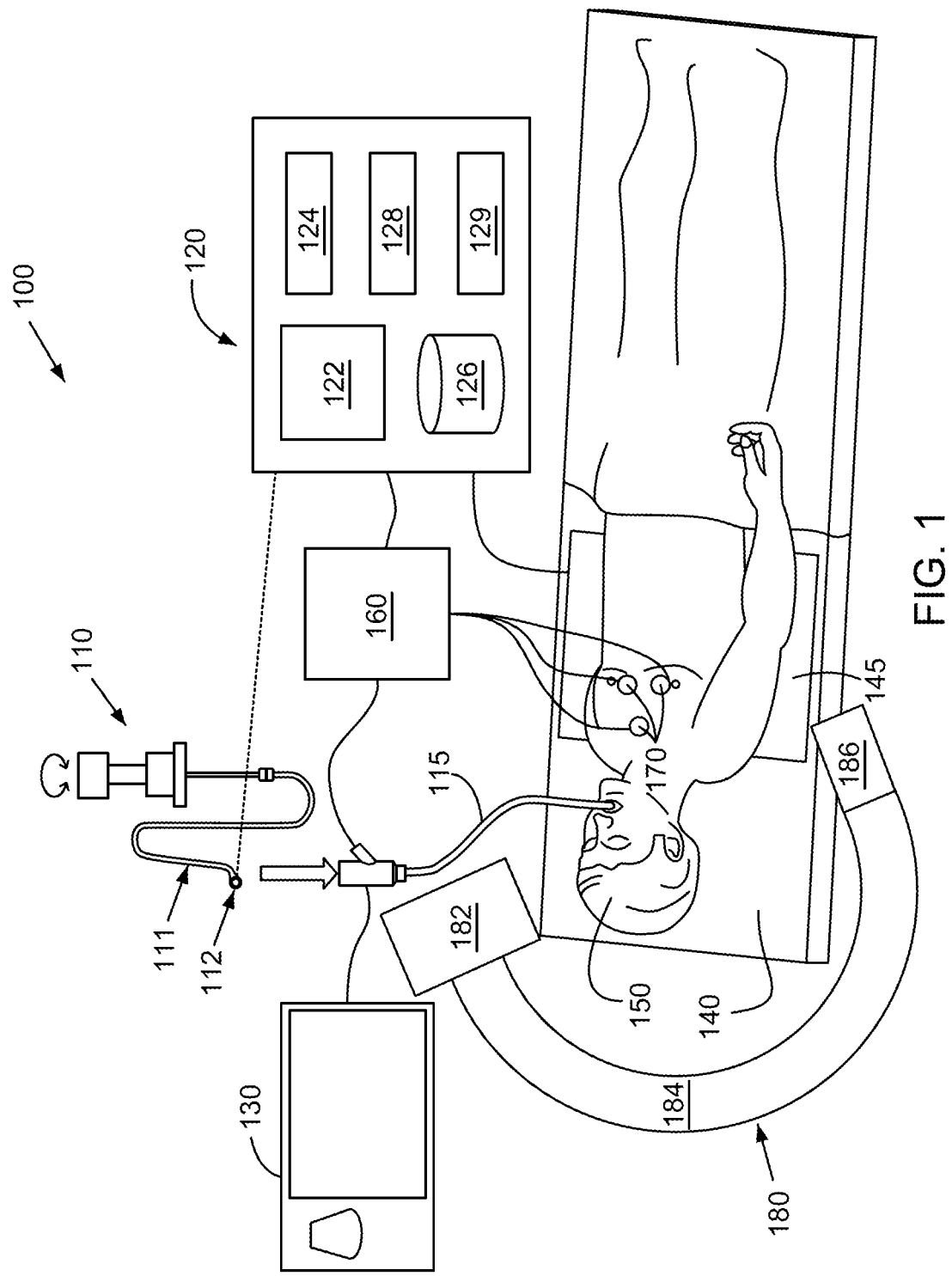
FIG. 1 is a diagram of an example electromagnetic navigation (EMN) system in accordance with this disclosure.

As described above, to accurately determine sensor location and/or orientation, a detailed map of electromagnetic (EM) field measurements at respective sensor locations is generated. Generating such a map, however, requires taking precise electromagnetic field measurements at, for example, hundreds of thousands or more locations within the expected electromagnetic volume.

The burden of generating electromagnetic field maps increases in circumstances where there are many antennae in the antenna assembly. For example, in order to enable an electromagnetic sensor to reach deeper portions of the body of the patient, and/or remain within the body during subsequent medical procedures without interfering with additional medical devices, it may be desirable to employ a small electromagnetic sensor, such as a single-coil electromagnetic sensor. However, to employ a small electromagnetic sensor for EMN while maintaining the ability to determine multiple (for example, five or six) degrees of freedom of the sensor, multiple antennae may be required to increase the number of radiated electromagnetic fields to be sensed. In such a case, the above-noted exhaustive mapping procedure may need to be conducted for each antenna assembly design. Moreover, given potential variations from manufacturing, the mapping procedure may even need to be completed for each instance of a specific antenna assembly design (i.e., each individual antenna assembly manufactured).

Making all of this more complex is the fact that many devices that may be found in a clinical space include metal components. These metal components when placed in proximity to an EM field can have Eddy currents induced in them, resulting in the generation of interfering EM fields. These interfering EM fields may be detected by the sensors and as a result the accuracy of the detected position and orientation of an EM sensor within the EM field suffers.

This disclosure relates to systems and methods for correcting errors in determining the position and orientation of electromagnetic sensors caused by magnetic fields induced in nearby metallic equipment, which interfere with mapped EM fields during an EMN procedure. By correcting for these interference magnetic fields, the accuracy of the determined position and orientation is increased.

In one application of the instant methods, an ultra-high density (UHD) EM field map is generated for a given EM field generator having multiple antennae. In general, for advanced EMN systems a UHD map is used to determine a location and/or an orientation of a sensor. The sensor typically includes multiple coils. The geometric configurations of the antennas that make up the EM field generator enable mathematical calculation of an expected or theoretical EM field strength at every UHD gridpoint within an EM volume. The EM sensor senses EM field strengths, and an EMN system 100 identifies the location and the orientation of the EM sensor based on the sensed EM field strengths and the expected EM field strengths of the UHD map.

The magnetic field will typically manifest itself in an additive field (in addition to the expected field strengths and directions at a given point). This additive field may have different gains for each of the antennas that make up the EM field generator, but the vector of the additive field will all be in the same direction across all antennas. Thus, in accordance with the disclosure, predetermined polynomials are evaluated using the first magnetic field vector measurements to obtain first position and orientation information for the plurality of sensors. Then, starting with the first position information, a simulated map is searched for position information of the sensors such that the difference between (a) the sum of simulated magnetic field vectors corresponding to the position information and interference magnetic field vectors, which is rotated according to orientation information, and (b) the second magnetic field vector measurements are minimized. In this manner, the interference magnetic field may be determined and corrected position information regarding the sensors may be obtained.

FIG. 1 illustrates an example electromagnetic navigation (EMN) system 100, which is configured to identify a location and/or an orientation of a medical device, or sensor thereof, navigating (e.g., to a target) within the patient's body by using an antenna assembly, which includes a plurality of antennas and generates EM fields. The EMN system 100 is further configured to augment computed tomography (CT) images, magnetic resonance imaging (MRI) images, or fluoroscopic images in navigation through patient's body toward a target of interest, such as a diseased portion in a luminal network of a patient's lung.

The EMN system 100 includes a platform 140 that is configured to provide a flat surface upon which the patient 150 lies during the EMN navigation procedure. The antenna assembly 145, which may also be referred to as an EM field generating device, is arranged upon the platform 140 or is included as a component of the platform 140. The antenna assembly 145 includes multiple antennas, such as planar loop antennas (not shown in FIG. 1). In some embodiments, the antenna assembly includes, on a single substrate, multiple planar antennas having characteristics, such as geometries and/or relative locations that are diverse from one another, that enable multiple (for example, six) degrees of freedom of a small electromagnetic sensor, such as a single-coil sensor, to be determined. Example aspects of the antenna assembly 145 are described in further detail below.

With the patient 150 lying upon the platform 140, the one or more processors 124 (or another signal generator not shown in FIG. 1) generate and provide to the antennas of the antenna assembly 145 one or more EM signals that are radiated by the antennas in a manner sufficient to surround a portion of the patient 150. In some aspects, the antenna assembly 145 includes a connector that has at least two terminals, and the trace of the antenna (not shown in FIG. 1) has two ends that are coupled to the two connector terminals, respectively, to form a signal communication path from the one or more processors 145 to the antenna.

The EMN system 100 also includes a catheter guide assembly 110, a bronchoscope 115, a computing device 120, a monitoring device 130, an EM field generator 140, a tracking device 160, and reference sensors 170. The bronchoscope 115 is operatively coupled to the computing device 120 and the monitoring device 130 via a wired connection (as shown in FIG. 1) or wireless connection (not shown in FIG. 1). The reference sensors 170 may include three patient sensors placed on the patient. One patient sensor may be placed on the sternum of the patient and the other two patient sensors may be placed on the ribs of the patient.

The bronchoscope 115 is inserted into the mouth of a patient 150 and captures images of the luminal network of the lung. In the EMN system 100, inserted into the bronchoscope 115 is a catheter guide assembly 110 for achieving access to the periphery of the luminal network of the lung of the patient 150. The catheter guide assembly 110 may include an extended working channel (EWC) 111 with an EM sensor 112 at the distal portion of the EWC 111. A locatable guide catheter (LG) may be inserted into the EWC 111 with another EM sensor at the distal portion of the LG. The EM sensor 112 at the distal portion of the EWC 111 or the LG is used to identify a location and/or an orientation of the EWC 111 or the LG while navigating through the luminal network of the lung. Due to the size restriction in the EWC 111 or the LG, in some embodiments, the EM sensor 112 may include only one single coil for detecting EM field strength of an EM field over the patient 150. However, the number of coils in the EM sensor is not limited to one but may be two or more.

The computing device 120, such as, a laptop, desktop, tablet, or other similar computing device, includes a display 122, one or more processors 124, memory 126, an AC current driver 127 for providing AC current signals to the antenna assembly 145, a network card 128, and an input device 129. The particular configuration of the computing device 120 illustrated in FIG. 1 is provided as an example, but other configurations of the components shown in FIG. 1 as being included in the computing device 120 are also contemplated. In particular, in some embodiments, one or more of the components (122, 124, 126, 127, 128, and/or 129) shown in FIG. 1 as being included in the computing device 120 may instead be separate from the computing device 120 and may be coupled to the computing device 120 and/or to any other component(s) of the system 100 by way of one or more respective wired or wireless path(s) to facilitate the transmission of power and/or data signals throughout the system 100. For example, although not shown in FIG. 1, the AC current driver 127 may, in some example aspects, be separate from the computing device 120 and may be coupled to the antenna assembly 145 and/or coupled to one or more components of the computing device 120, such as the processor 124 and the memory 126, by way of one or more corresponding paths.

In some aspects, the EMN system 100 may also include multiple computing devices, wherein the multiple computing devices are employed for planning, treatment, visualization, or helping clinicians in a manner suitable for medical operations. The display 122 may be touch-sensitive and/or voice-activated, enabling the display 122 to serve as both input and output devices. The display 122 may display two-dimensional (2D) images or three-dimensional (3D) model of a lung to locate and identify a portion of the lung that displays symptoms of lung diseases.

The one or more processors 124 execute computer-executable instructions. The processors 124 may perform image-processing functions so that the 3D model of the lung can be displayed on the display 122 or location algorithm to identify a location and an orientation of the EM sensor 112. In embodiments, the computing device 120 may further include a separate graphic accelerator (not shown) that performs only the image-processing functions so that the one or more processors 124 may be available for other programs. The memory 126 stores data and programs. For example, data may be mapping data for the EMN or any other related data such as a UHD map, image data, patients' medical records, prescriptions and/or history of the patient's diseases.

The ultra-high density (UHD) map may include multiple gridpoints in a fine coordinate system of the EM volume in which a medical device (e.g., the EWC 111, LG, treatment probe, or other surgical devices) is to be navigated, and expected EM field strengths at each of the plurality of gridpoints. As the EM sensor 112 senses an EM field strength at a given point, the one or more processors 124 identifies the location of the EM sensor 112 within the EM volume based on the sensed EM field strength and the expected EM field strengths in the UHD map. Further, an orientation of the medical device may be also calculated based on the sensed EM field strength and the UHD map.

As shown in FIG. 1, the EM field generator 140 is configured to provide a flat surface for the patient 150 to lie upon and includes an antenna assembly 145. When the patient 150 lies upon on the EM field generator 140, the antenna assembly 145 generates an EM field sufficient to surround a portion of the patient 150 or the EM volume. The antenna assembly 145 includes a plurality of antennas, each of which may include a plurality of loops. Each antenna is configured to generate an EM waveform having a corresponding frequency. The number of antennas may be at least six and in at least one embodiment is nine so that nine different EM waveforms are generated.

A time multiplexing method may be employed in generating the EM waveforms. For example, the antennas of the antenna assembly 145 may generate EM waveforms with the same frequency at different times during a period. Alternatively, frequency multiplexing method may be employed, where each antenna generates EM waveform having a frequency different from each other. In still another configuration, a combination of the time multiplexing and frequency multiplexing methods may be employed. The antennas are grouped into more than one group. Antennas in the same group generate EM waveforms having the same frequency but at different times. Antennas in different groups may generate EM waveforms having different frequencies from each other. Corresponding de-multiplexing method is to be used to separate EM waveforms.

Each antenna may have a geometric configuration (for instance, where the antennae each have geometric configurations based on linear portions of printed circuit board (PCB) traces or wires, which facilitate use of the superposition principle in computing the total contribution of the fields generated by way of each antenna to the total combined EM field within the volume) so that each portion of the plurality of loops can be expressed as mathematical relationships or equations. The magnetic field can thus be computed for each trace on the antenna and the contributions from all traces can be summed. Based on this geometric configuration, expected EM field strength at each gridpoint in the UHD map can be theoretically or mathematically calculated via a simulation.

In general, the computing device 120 of the EMN system 100 controls the antenna assembly 145 embedded in the EM field generator 140 to generate an EM field, receives sensed results from the EM sensor 112, and determines a location and an orientation of the EM sensor 112 in the EM volume.

The computing device 120 includes a clock, which generates a clock signal used for generating the EM field and sampling the sensed results. Since the same clock signal is used for generating the EM field and sampling the sensed EM field, synchronization between the magnetic field generation circuitry (e.g., a waveform generator) and the waveform acquisition circuitry (e.g., a digitizer) may be achieved. In other words, when the clock provides a clock signal to the waveform generator and the digitizer, the EM waveforms generated by the antenna assembly 145 are digitally sampled by digitizer substantially at the same time. The digitizer may include an analog-to-digital converter (ADC, which is not shown) to digitally sample the sensed results and an amplifier (which is not shown) to amplify the magnitude of the sensed result so that the magnitude of the sensed results is within the operable range of the ADC. In an aspect, the digitizer may include a pre-amplifier and post-amplifier so that the magnitude of the sensed result is amplified to be within the operable range of the ADC by the pre-amplifier and digital samples are also amplified to the magnitude of the sensed result by the post-amplifier.

A demodulator demodulates the digital samples to remove unwanted signals (e.g., noises) and to restore the EM waveforms, which have been generated by the antenna assembly 145. The demodulator may use time de-multiplexing method, frequency de-multiplexing method, or combination of both to separate and identify the EM waveforms depending on the method used by the antennas of the antenna assembly 145 to generate the EM waveforms, and to determine EM field strength affected by each of the antenna of the antenna assembly 145.

For example, when the antenna assembly 145 includes six antennas, the demodulator is capable of identifying six EM field strengths, which is sensed by the EM sensor 112, for the six antennas, respectively. In a case when the number of antennas is nine, the outputs of the demodulator may be expressed in a form of a nine by one matrix. Based on the modulation method (e.g., time multiplexing, frequency multiplexing, or a combination thereof) utilized by the antennas, the demodulator demodulates the sensed result.

For example, when the antennas of the antenna assembly 145 utilize frequency multiplexing, the demodulator may use a set of finely tuned digital filters. Orthogonal frequency division multiplexing may also be utilized, in which the EM field and sampling frequencies are chosen in such a way that only the desired frequency from a specific antenna is allowed to pass while other frequencies are precisely stopped. In an aspect, the demodulator may use a multiple tap orthogonal frequency matched filter, in which the digital filter for a specific frequency is tuned to the desired demodulation window.

The memory 126 may store data and programs related to identification of a location and an orientation. The data includes an ultra-high density (UHD) map, which includes a plurality of gridpoints for the EM volume and expected EM field strengths at the gridpoints. The UHD map may be based on three-axis coordinate system, where each gridpoint has three coordinates corresponding to the three axes, respectively. In this case, the expected EM field strength at each gridpoint may include one EM field strength value along each axis for each EM waveform. For example, if there are nine antennas generating nine different EM waveforms, each of which having a separate frequency, and three axes are x, y, and z axes, the expected EM field strength may include nine EM field strength values along the x axis, nine EM field strength values along the y axis, and nine EM field strength values along the z axis, at each gridpoint. Such expected EM field strength at each gridpoint may be expressed in a nine by three matrix form.

The UHD map may be made with computations in a simulation, which includes theoretically calculated EM field strengths at each axis at each gridpoint in the fine coordinate system, and measurement, which includes measurements at each axis at each gridpoint in the coarse coordinate system. The fine coordinate system includes all the gridpoints in the coarse coordinate system and the gridpoints of the fine coordinate system are more finely distributed than those of the coarse coordinate system. By using the geometric configuration of the antennas of the antenna assembly 145, measurement may not have to be made with the fine coordinate system. Rather, the measurement may be made in the coarse coordinate system and theoretical computations may be made in the fine coordinate system. By combining the measurements in the coarse coordinate system with the theoretical computations in the fine coordinate system, the UHD map may be generated. Generation of the UHD map based on the measurement and calculations will be described in further detail with respect to FIG. 2 below.

After passage of time or due to foreign objects near the EMN system 100, measurements by the EM sensor 112 or other hardware may need to be calibrated. Such calibration data may be also stored in the memory 126 in a form of sensor calibration and hardware calibration.

When the computing device 120 receives measurement data from the EM sensor 112 via the demodulator, the computing device 120 uses the location algorithm, which is also stored in the memory 126, with the UHD map to identify the location and the orientation of the EM sensor 112.

The location algorithm may utilize any error minimization algorithm in identifying the location and the orientation of the EM sensor 112. For example, Levenberg-Marquardt algorithm may be employed to minimize errors between (a) the expected magnetic field strengths of the UHD map in combination with magnetic interference field strengths, and (b) the sensed results. Other error minimization methods or algorithms, which a person having ordinary skill in the art can readily appreciate, may also be utilized without departing from the scope of this disclosure.

The memory 126 further includes applications, which can be utilized by the computing device 120 of the EMN system 100 and which uses information regarding the location and the orientation of the EM sensor 112. Such application may be a displaying application, which displays a graphical representation of a medical device, on which the EM sensor 112 is mounted or installed, at the location of the EM sensor 112 and along the orientation of the EM sensor 112 in the EM volume, an application for treatment, which determines whether a medical device is near a target of interest, or any other applications, which use the location and the orientation of the EM sensor 112.

The EM field generator 140 produces EM fields around the patient. These EM fields will induce currents in any metal object that might come in proximity to the EM field, such as a fluoroscope 180. The fluoroscope 180 illustrated in FIG. 1 is a C-mount fluoroscope which includes an x-ray source 186 and an image acquisition module 182 at opposite ends of a C-mount 184. The image acquisition module 182 may include an image intensifier (not shown), a front face (not shown) which faces the x-ray source 186, and a CCD camera (not shown), mounted on the end of the image intensifier that is opposite front face, for acquiring images that are intensified by the image intensifier. The image intensifier may be housed in a cylindrical housing. In addition, the image acquisition module 182 may include an annular compensator (not shown). The EM fields generated by the EM field generator may induce Eddy currents in the various components of the fluoroscope. For example, Eddy currents may be induced in the image intensifier of the image acquisition module 182.

In practice, the fluoroscope 180 is mobile and may be placed in different locations within a procedure room, but, as described above, includes a number of large metal components. Thus, when a fluoroscope is brought into the EM field, such as when navigation to a desired target is near its end and real-time imaging is desired, the act of moving the fluoroscope can degrade the accuracy of the detected location of the EM sensor 112 within the EM field.

Though the EM sensor 112 has been referred to, reference sensors 170 placed on the exterior of the patient and referred to collectively as the patient sensor triplet (PST) are of similar construction and provide the primary source of data to computing device 120 for dynamic interference correction.

Because there are, in one example, nine antennae that make up the EM field generator, and each is generating its own EM field, each of these fields will induce a separate current in a metal object such as the fluoroscope. Each of these currents will produce an interfering EM field. These fields will be identifiable at every position in the sensing volume produced by the EM field generator 140 as an additive field. This additive field will appear in all nine frequencies of the measured magnetic fields used to determine the location of the reference sensors 170 in the map.

In the case where the navigation system is used with a Fluoroscope, the magnetic interference generated by the Fluoroscope primarily impacts the patient sensors because the Fluoroscope is closest source of potential magnetic interference to the patient sensors. The patient sensors form the body coordinate system. When the positions of the patient sensors are inaccurate, the positions of the catheter sensor and the EWC sensor in the body coordinates are inaccurate even though their position in antenna coordinates are accurate. Thus, the computing device solves for interference for each of the three patient sensors. Optionally, the computing device solves for interference for a catheter sensor connected to the navigation system. In general, when solving for the magnetic interference on the patient sensors, the position of the EWC sensor on the CT image is more accurate. Thus, the computing device does not solve for interference on the EWC sensor.

To solve for the magnetic interference on the patient sensors 170, each of which may have three channels corresponding to three sensor coils disposed orthogonal to each other, and optionally the catheter sensor, starting positions and orientations of the patient sensors 170 are computed using 3 antenna (disregarding the other 6 antennas) and using polynomials found in a mapping process. Next, a Levenberg-Marquadt search is performed to try to find on a ultra-high definition (UHD) map the 3 (or 4) sensor positions such that the sum of the magnetic field vectors from the map (interpolated to the sensor positions) and the solved magnetic interference vectors, which is rotated according to the solved sensors orientations (to get the sum in the sensors' coordinate systems) would be the closest to the actual sensor measurements or pickups.

The Levenberg-Marquadt search assumes that the Eddy currents induced in the source of dynamic interference, e.g., a Fluoroscope, are flowing in the same route or path for all magnetic fields generating the Eddy currents. The route or path may be a loop in any given shape, such as a circle or ring, a square, a rectangle, or a star. For example, in the case of fluoroscope 180, the induced currents may flow in a metal ring of the fluoroscope image intensifier. Even though the magnetic fields are in different orientations, the Eddy currents are induced in the same route. Thus, the induced Eddy currents generate nine magnetic interference vectors that, for a particular sensor position, all share the same direction. The amplitude ratios are determined according to the induced Eddy currents. For a second sensor, all amplitude ratios are the same as for a first sensor, and all magnetic interference vectors are in the same direction, but are in a different direction than the direction of all the magnetic interference vectors at the first sensor.

Accordingly, when the computing device solves for the magnetic interference on the 3 or 4 sensors, the computing device solves for eight global ratios. This assumes that the amplitude of a first magnetic interference vector at a first frequency is 1 and that the eight global ratios are the amplitudes of the other magnetic interference vectors at eight other frequencies relative to the amplitude of the first magnetic interference vector at the first frequency. Thus, for each sensor, the computing device solves for its position and orientation and the interference vectors (each of which comprises three coordinates) of the first frequency and the other eight frequencies. The other eight interference vectors are computed by multiplying the interference vector of the first frequency by the eight global ratios. In summary, for an example navigation system including three patient sensors and nine antennae, the computing device solves for 35 variables (that is, (6 degrees of freedom of the source of dynamic interference+3 coordinates of an interference vector)*3 patient sensors+8 common or global ratios) based on 81 sensor data points (that is, 3 sensed coordinates*9 magnetic fields*3 patient sensors).

A high definition (HD) map provides a low-resolution grid of positions (e.g., every 5 mm). Each grid position includes as many magnetic vectors as there are antennas in the antenna assembly 145. For example, if there are nine antennae, there will be 9 magnetic field vectors at each grid position. In accordance with this disclosure, a method for defining an ultra-HD (UHD) map, which provides a high-resolution grid of positions (e.g., every 1 mm), for a given system is described. The starting point for the UHD map is a calculated or simulated UHD map that can be derived from the construction or geometry of the antenna assembly 145 and the driving frequencies of the individual antenna using the Biot-Savart law for mapping magnetic fields.

In the process of installing an individual EM board 140 (including antenna assembly 145) as part of the EMN system 100 in a specific location, a mapping of the EM field generated by the EM board 140 is undertaken. This in-situ mapping is necessary to account for eddy currents that can be induced in the metal frames of surgical beds and other stationary metal components that are within the magnetic field. These eddy currents in the metal components, particularly the surgical bed, generate their own magnetic fields, referred to as additive magnetic fields. These additive magnetic fields are at the same frequencies as the magnetic fields generated by the antenna assembly 145.

Figure 2:
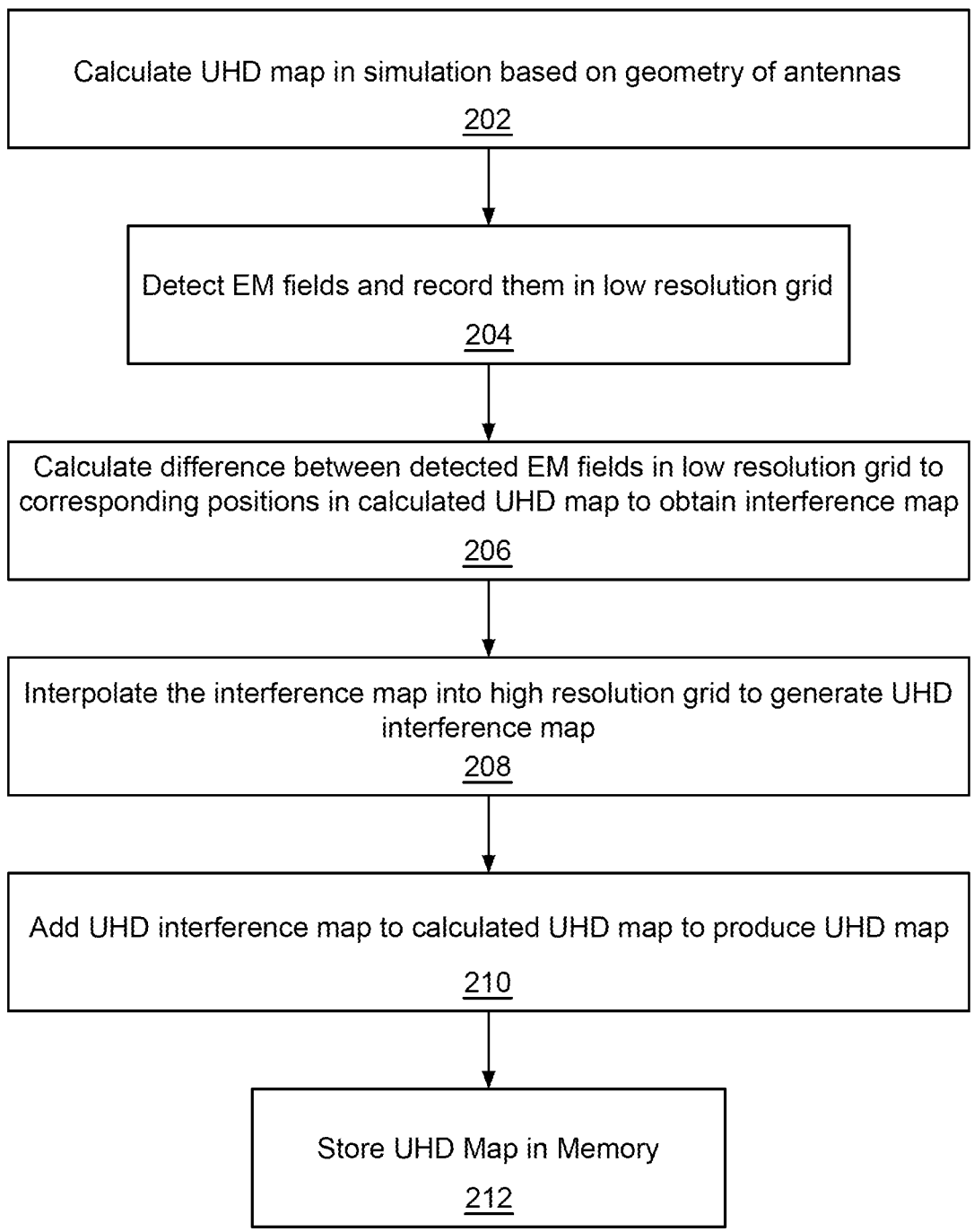
FIG. 2 is a flow diagram of a method of generating a simulated map in accordance with this disclosure.

FIG. 2 illustrates an example method 200 of generating a high-resolution map for use by magnetic interference correction methods of this disclosure. In accordance with the generation of the UHD map, actual readings of the EM fields generated by the nine antennae are taken using an EM field sensor at block 202 and associated with positions in a low-resolution grid of positions. In one example, the low-resolution grid is a 9×9×9 matrix of positions. The EM field measurements at each of these positions is compared by the processor 124 to that of the simulated UHD map at block 204. The difference between the detected magnetic fields of the low-resolution gird and the magnetic fields of the simulated UHD map at each of the positions of the low-resolution grid, represents the interference (e.g., bed interference) that is generated by the eddy currents (the additive magnetic fields) and is calculated at block 206.

The low-resolution grid (i.e., the sampling points) is spaced over the entirety of the EM board 140. Because the interference or additive magnetic fields do not dramatically change between the sample points, the processor 124 is able to interpolate, at block 208, the low-resolution bed interference map into a high-resolution grid having the same number of positions as the calculated UHD map to generate a high definition map of the interference. The UHD map of the interference is then added to the simulated UHD map to provide an adjusted UHD map at block 210. This adjusted UHD map is saved in memory at block 212 and is then used for future navigation using the EMN system 100.

Each of the multiple antennas may be configured to radiate a separate EM field, for example, using frequency division multiplexing and/or time division multiplexing controlled by the processors 124 or by another generator. For example, the antennas, in some aspects, may be configured to radiate multiple EM fields sufficient in number and/or sufficient in diversity of characteristics (such as frequency, time, modulation scheme, and/or the like) to enable a single-coil electromagnetic sensor mounted on the EWC 111, or on any other medical device, to be used to determine the location and/or the orientation of the sensor, the EWC 111, and/or the medical device. The antenna assembly 145 may, for instance, include six to nine or more loop antennas. In some embodiments, for each of the loop antennas, the distances between its adjacent loops increase as the loops become larger. For example, for each of the planar antennas, respective distances between adjacent pairs of loops may increase in a direction from an innermost one of the loops to an outermost one of the loops of the respective planar antenna.

Each of the antennas of the designed antenna assembly can be printed, deposited, or fabricated on a respective substrate layer and can be used as the EM field generator 145 of the EMN system 100 of FIG. 1. Further, by virtue of employing straight linear portions to constitute the loop antennas, electromagnetic fields generated by each linear portion can be theoretically and accurately calculated using the Biot-Savart-Laplace law at any point in the EM volume.

Figure 3:
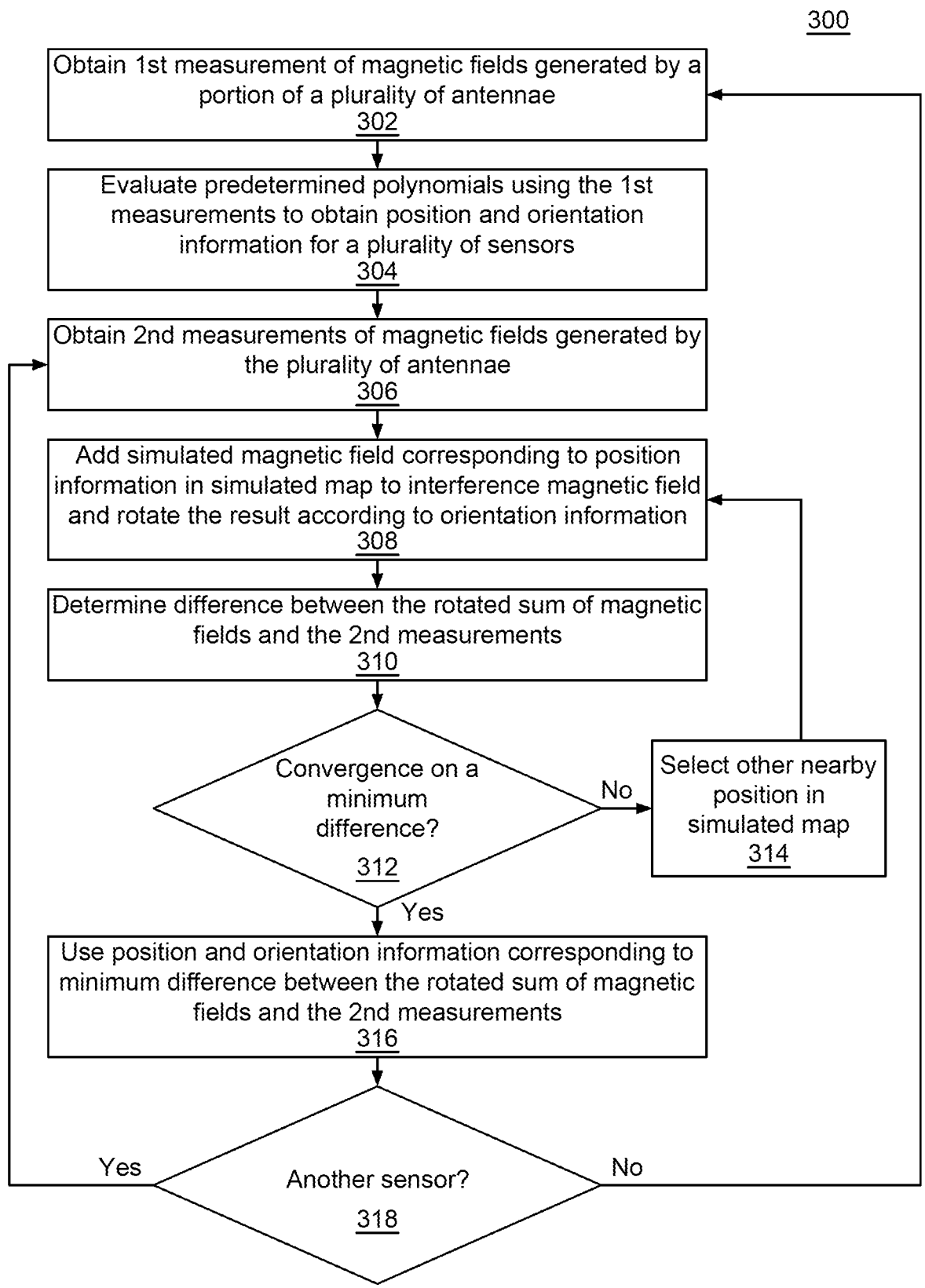
FIG. 3 is a flow diagram of a method of magnetic interference correction in accordance with this disclosure.

FIG. 3 is a flow diagram of a method of magnetic interference correction in accordance with an embodiment of this disclosure. At block 302, a computing device obtains, from three patient sensors, first measurements of magnetic fields generated by a portion of a plurality of antennae of an antenna assembly (e.g., three antenna our of nine antennae of an antenna assembly) disposed under the patient. At block 304, the computing device evaluates predetermined polynomials using the first measurements to obtain position and orientation information for a plurality of sensors, such as three patient sensors. The predetermined polynomials provide a relationship between magnetic field vector measurements obtained by the three patient sensors and position and orientation information of the three patient sensors. The predetermined polynomials are determined based on calibration measurements of the magnetic fields generated by the three antennae at known positions and orientations of the patient sensors.

At block 306, the computing device obtains, from a plurality of sensors, such as three patient sensors, second measurements of magnetic fields generated by a plurality of antennae, such as nine antennae, of the antenna assembly. At block 308, the computing device adds a simulated magnetic field corresponding to position information in a simulated map to an interference magnetic field and rotates the result according to the orientation information. At block 310, the computing device determines the difference between the rotated sum of magnetic fields and the second measurements of the magnetic fields generated by the nine antennae. At block 312, the computing device determines whether there is convergence on a minimum difference. If there is no convergence, the computing device selects another nearby position in the simulated map at block 312 and repeats blocks 308-312. In some embodiments, blocks 308-314 may be performed according to a Levenberg-Marquadt search algorithm. In other embodiments, blocks 308-314 may be performed according to another search algorithm that seeks to minimize the difference between the rotated sum of magnetic fields and the second measurements.

If there is convergence on a minimum difference between the rotated sum of magnetic fields and the second measurements, the computing device uses the position and orientation information of the patient sensor corresponding to the minimum difference between the rotated sum of magnetic fields and the second measurements at block 316. At block 318, the computing device determines whether there is another patient sensor whose magnetic field measurements need to be processed in order to determine the corrected position and orientation information of the other patient sensor. If there is another patient sensor whose magnetic field measurements need to be processed, the computing device returns to block 306 to obtain, from the other patient sensor, second measurements of the magnetic fields generated by the nine antenna of the antenna assembly. If there is not another patient sensor whose magnetic field measurements need to be processed, the computing device returns to block 302 to repeat the method 300, as the patient sensors and/or the fluoroscope (or other equipment near the patient sensors) may have moved to different positions and/or orientations.

Figure 4:
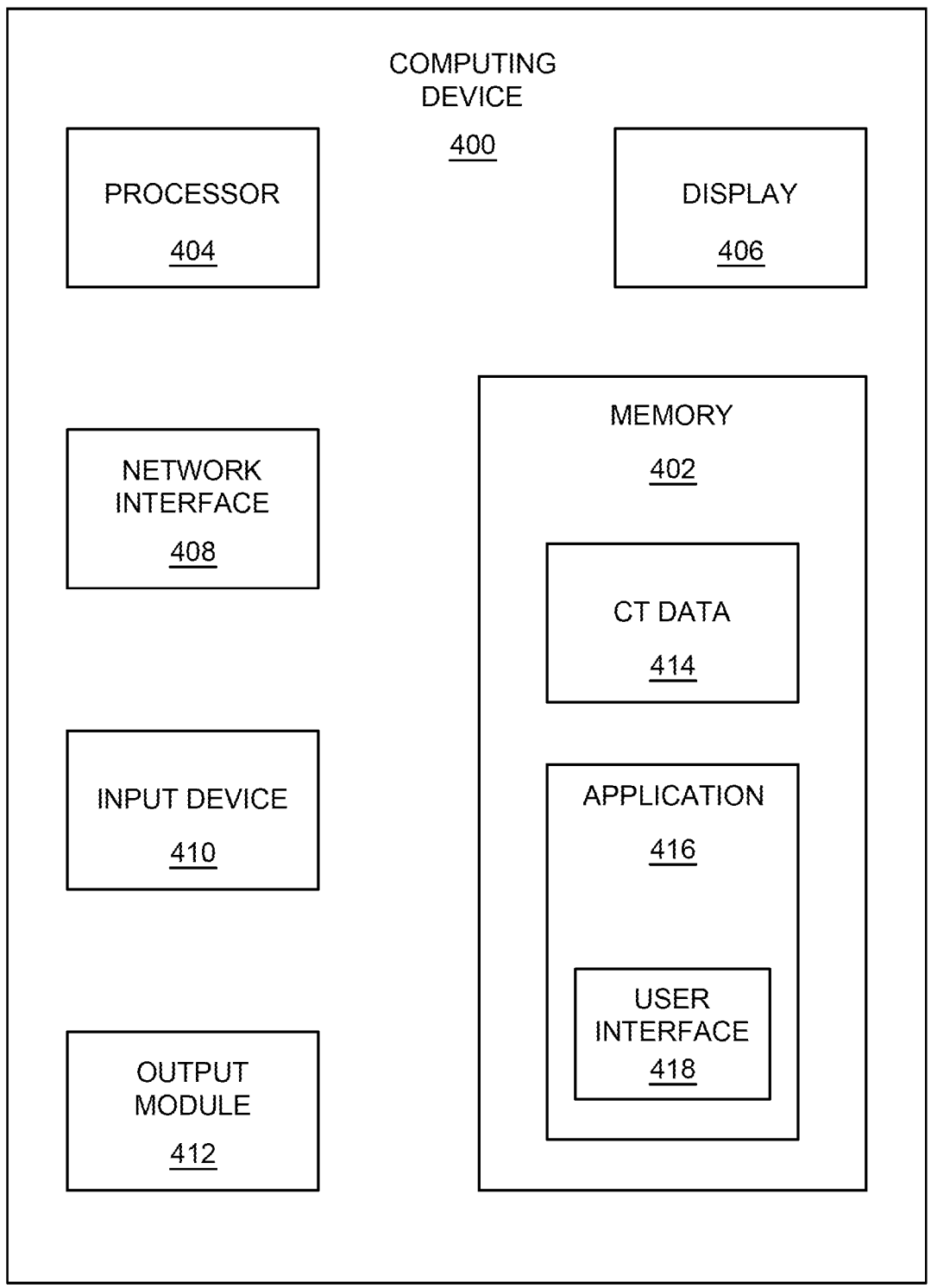
FIG. 4 is a block diagram of the computing device of FIG. 1 in accordance with embodiments of the disclosure.

Turning now to FIG. 4, there is shown a block diagram of a computing device 400, which can be used as the EMN system 100, the control workstation 102, the tracking device 160, and/or a computer performing the methods 200 and 300 of FIGS. 2 and 3. The computing device 400 may include one or more of each of the following components: a memory 402, a processor 404, a display 406, network interface controller 408, an input device 410, and/or an output module 412.

The memory 402 includes any non-transitory computer-readable storage media for storing data and/or software that is executable by the processor 404 and which controls the operation of the computing device 400. In an embodiment, the memory 402 may include one or more solid-state storage devices such as flash memory chips. Alternatively, or in addition to the one or more solid-state storage devices, the memory 402 may include one or more mass storage devices connected to the processor 404 through a mass storage controller (not shown in FIG. 4) and a communications bus (not shown in FIG. 4). Although the description of computer-readable media contained herein refers to a solid-state storage, it should be appreciated by those skilled in the art that computer-readable storage media can be any available media that can be accessed by the processor 404. That is, computer readable storage media include non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 400.

The memory 402 may store application 416 and/or CT data 414. The application 416 may, when executed by the processor 404, cause the display 406 to present user interface 418 on the display 406.

The processor 404 may be a general purpose processor, a specialized graphic processing unit (GPU) configured to perform specific graphics processing tasks while freeing up the general purpose processor to perform other tasks, a programmable logic device such as a field programmable gate array (FPGA) or complex programmable logic device (CPLD), and/or any number or combination of such processors or devices configured to work independently or cooperatively.

The display 406 may be touch-sensitive and/or voice-activated, enabling the display 406 to serve as both an input and output device. Alternatively, a keyboard (not shown), mouse (not shown), or other data input devices may be employed.

The network interface 408 may be configured to connect to a network, such as a local area network (LAN) including a wired network and/or a wireless network, a wide area network (WAN), a wireless mobile network, a Bluetooth network, and/or the Internet. For example, the computing device 400 may receive the predetermined functions or polynomials and perform the method 300 of FIG. 3 to search for a position and orientation of a patient or catheter sensor. The computing device 400 may receive updates to its software, for example, application 416, via the network interface controller 408. The computing device 400 may also display notifications on the display 406 that a software update is available.

In another aspect, the computing device 400 may receive computed tomographic (CT) image data of a patient from a server, for example, a hospital server, Internet server, or other similar servers, for use during surgical planning. Patient CT image data may also be provided to the computing device 400 via a removable memory (not shown in FIG. 4).

Input device 410 may be any device by means of which a user may interact with the computing device 400, such as, for example, a mouse, keyboard, foot pedal, touch screen, and/or voice interface.

Output module 412 may include any connectivity port or bus, such as, for example, parallel ports, serial ports, universal serial busses (USB), or any other similar connectivity port known to those skilled in the art.

The application 416 may be one or more software programs stored in the memory 402 and executed by the processor 404 of the computing device 400. During a calibration phase, one or more software programs in the application 416 may be loaded from the memory 402 and executed by the processor 404 to determine functions or polynomials that provide a relationship between (a) magnetic field vector measurements obtained by the patient sensors and (b) position and orientation information of the patient sensors based on calibration measurements of the magnetic fields generated by a portion of the antennae at known positions and orientations of the patient sensors. In some embodiments, during a planning phase, one or more programs in the application 416 guides a clinician through a series of steps to identify a target, size the target, size a treatment zone, and/or determine an access route to the target for later use during the navigation or procedure phase. In some other embodiments, one or more software programs in the application 416 may be loaded on computing devices in an operating room or other facility where surgical procedures are performed, and is used as a plan or map to guide a clinician performing a surgical procedure, but without any feedback from the medical device used in the procedure to indicate where the medical device is located in relation to the plan.

The application 416 may be installed directly on the computing device 400, or may be installed on another computer, for example a central server, and opened on the computing device 400 via the network interface 408. Application 416 may run natively on the computing device 400, as a web-based application, or any other format known to those skilled in the art. In some embodiments, the application 416 will be a single software program having all of the features and functionality described in this disclosure. In other embodiments, the application 416 may be two or more distinct software programs providing various parts of these features and functionality. For example, the application 416 may include one software program for determining the functions or polynomials in a calibration phase, another one for taking magnetic field measurements from the patient sensors and/or catheter sensor, and a third program for performing a search on the UHD map. In such instances, the various software programs forming part of the application 416 may be enabled to communicate with each other and/or import and export various data including settings and parameters relating to the patient sensors. For example, the predetermined functions or polynomials generated by one software program may be stored and exported to be used by a second software program that evaluates the predetermined functions or polynomials to obtain initial position and orientation information, and the initial position and orientation information may be also stored and exported to be used by a searching software program to search a UHD map starting with the initial position and orientation information.

The application 416 may communicate with a user interface 418 which generates a user interface for presenting visual interactive features to a user, for example, on the display 406 and for receiving input, for example, via a user input device. For example, user interface 418 may generate a graphical user interface (GUI) and output the GUI to the display 406 for viewing by a user.

In a case that the computing device 400 may be used as the EMN system 100, the control workstation 102, or the tracking device 160, the computing device 400 may be linked to the monitoring device 130, thus enabling the computing device 400 to control the output on the monitoring device 130 along with the output on the display 406. The computing device 400 may control the monitoring device 130 to display output which is the same as or similar to the output displayed on the display 406. For example, the output on the display 406 may be mirrored on the monitoring device 130. Alternatively, the computing device 400 may control the monitoring device 130 to display different output from that displayed on the display 406. For example, the monitoring device 130 may be controlled to display guidance images and information during the surgical procedure, while the display 406 is controlled to display other output, such as configuration or status information of an electrosurgical generator (not shown in FIG. 1).

The application 416 may include one software program for use during the planning phase, and a second software program for use during the navigation or procedural phase. In such instances, the various software programs forming part of application 416 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of this disclosure. For example, various steps of the methods described herein may be implemented concurrently and/or in an order different from the example order(s) described herein.

What is claimed is:

1. A system comprising:
  a plurality of antennae configured to generate a plurality of magnetic fields at different frequencies;
  a plurality of sensors configured to measure the plurality of magnetic fields; and
  a computing device configured to:
    obtain first magnetic field vector measurements from the plurality of sensors for a portion of the plurality of antennae;
    evaluate predetermined functions using the first magnetic field vector measurements to obtain first position and orientation information for the plurality of sensors;
    obtain second magnetic field vector measurements from the plurality of sensors for the plurality of antennae; and
    search, starting with the first position information, a simulated map for second position information of the plurality of sensors such that the difference between (a) the sum of simulated magnetic field vectors corresponding to the second position information and a plurality of interference magnetic field vectors, the sum being rotated according to orientation information, and (b) the second magnetic field vector measurements are minimized.

2. The system of claim 1, wherein the plurality of sensors includes three patient sensors.

3. The system of claim 2, wherein the plurality of sensors further includes a catheter sensor.

4. The system of claim 1, wherein the computing device is further configured to determine the plurality of interference magnetic field vectors, which includes determining three coordinates of an interference magnetic field vector for each of the plurality of sensors at one frequency of the magnetic field generated by one antenna of the plurality of antennae and determining a plurality of ratios for a respective plurality of other frequencies of magnetic fields generated by other antennae of the plurality of antennae.

5. The system of claim 1, wherein the plurality of antennae includes nine antennae.

6. The system of claim 1, wherein the portion of the plurality of antennae includes three antennae.

7. The system of claim 1, wherein searching the simulated map includes performing a Levenberg-Marquardt search.

8. The system of claim 1, further comprising a medical device, which generates the plurality of interference magnetic field vectors from Eddy currents induced in the medical device by a respective plurality of magnetic fields generated by the respective plurality of antennae.

9. The system of claim 8, wherein the medical device is a Fluoroscope or a robotic arm.

10. The system of claim 1, wherein the computing device is further configured to determine functions that provide a relationship between (a) magnetic field vector measurements obtained by the plurality of patient sensors and (b) position and orientation information of the plurality of patient sensors based on calibration measurements of the magnetic fields generated by a portion of the plurality of antennae at known positions and orientations of the plurality of patient sensors.

11. A method comprising:
  obtaining, from a plurality of sensors, measurements of first magnetic fields generated by a portion of a plurality of antennae;
  evaluating predetermined functions using the first magnetic field measurements to obtain first position and orientation information for the plurality of sensors;
  obtaining second magnetic field measurements from the plurality of sensors for the plurality of antennae; and searching, starting with the first position information, a simulated map for second position information of the plurality of sensors such that the difference between (a) the sum of simulated magnetic field corresponding to the second position information and the interference magnetic field, the sum being rotated according to orientation information, and (b) the second magnetic field measurements is minimized.

12. The method of claim 11, wherein the plurality of sensors include three patient sensors.

13. The method of claim 11, wherein determining the plurality of interference vectors includes determining three coordinates of an interference vector for each of the plurality of patient sensors at one frequency of a magnetic field generated by one antenna of the plurality of antennae and determining a plurality of ratios for a respective plurality of other frequencies of magnetic fields generated by other antennae of the plurality of antennae.

14. The method of claim 11, wherein the plurality of antennae includes nine antennae.

15. The method of claim 11, wherein the portion of the plurality of antennae includes three antennae.

16. The method of claim 11, wherein searching the simulated map includes performing a Levenberg-Marquardt search.

17. The method of claim 11, further comprising determining functions that provide a relationship between (a) magnetic field vector measurements obtained by the plurality of patient sensors and (b) position and orientation information of the plurality of patient sensors based on calibration measurements of the magnetic fields generated by a portion of the plurality of antennae at known positions and orientations of the plurality of patient sensors.

18. The method of claim 11, wherein the simulated map is an ultra-high definition (UHD) map, and wherein the method further comprises calculating the UHD map based on geometry of the plurality of antennae and driving frequencies of each of the plurality of antennae.

19. The method of claim 18, further comprising:
interpolating a low-resolution interference map into a high-resolution grid having the same number of positions as the simulated UHD map to generate a UHD map of interference; and
combining the simulated UHD map with the UHD map of the interference to generate an adjusted simulated UHD map.

20. A method comprising:
measuring, by a plurality of sensors, a first magnetic field generated by a first plurality of antennae;
evaluating polynomials based on the first magnetic field to obtain position and orientation information for the plurality of sensors;
measuring, by the plurality of sensors, a second magnetic field generated by a second plurality of antennae; and
summing an interference magnetic field and a simulated magnetic field corresponding to position information in a simulated map to obtain a third magnetic field;
rotating the third magnetic field according to the orientation information;
determining a difference between the second magnetic field and the rotated magnetic field;
determining that the difference converges on a minimum difference; and
in response to determining that the difference converges on the minimum difference, using position and orientation information corresponding to the minimum difference.

* * * * *